United States Patent
Rozier et al.

[11] Patent Number: 5,167,240
[45] Date of Patent: Dec. 1, 1992

[54] INFUSION SITE GUARD

[75] Inventors: Betty M. Rozier, Hazelwood; Lisa M. Vallino, St. Louis, both of Mo.

[73] Assignee: Progressive IV's, Inc., Hazelwood, Mo.

[21] Appl. No.: 736,241

[22] Filed: Jul. 26, 1991

[51] Int. Cl.⁵ .............................. A61F 13/00
[52] U.S. Cl. .............................. 128/888; 128/846; 128/878
[58] Field of Search ......... 128/877, 887, 888, DIG. 6, 128/DIG. 26, 846, 857, 858, 869, 878, 879

[56] References Cited

U.S. PATENT DOCUMENTS

| | | | |
|---|---|---|---|
| 1,709,046 | 4/1929 | Throgmorton . | |
| 3,176,686 | 4/1965 | Barnes | 128/846 |
| 3,194,235 | 7/1965 | Cooke | 128/888 |
| 3,722,508 | 3/1973 | Roberts | 128/133 |
| 3,900,026 | 8/1975 | Wagner | 128/133 |
| 3,954,105 | 5/1976 | Nordby et al. | 128/275 |
| 4,517,971 | 5/1985 | Sorbonne | 128/133 |
| 4,626,246 | 12/1986 | Verkade | 604/174 |
| 4,633,863 | 1/1987 | Filips et al. | 128/165 |
| 4,679,553 | 7/1987 | Proulx et al. | 128/133 |
| 4,856,535 | 8/1989 | Forbes | 128/857 |
| 4,870,976 | 10/1989 | Denny | 128/877 |
| 4,898,587 | 2/1990 | Mera | 128/DIG. 26 X |
| 4,919,150 | 4/1990 | Grant | 128/877 |
| 4,976,698 | 12/1990 | Stokley | 604/174 |
| 5,018,534 | 5/1991 | Grant | 128/877 |

Primary Examiner—Robert A. Hafer
Assistant Examiner—Sam Rimell
Attorney, Agent, or Firm—Grace J. Fishel

[57] ABSTRACT

An infusion site guard for use at all peripheral and central venipuncture infusion sites and on pediatric and adult patients. The guard is a hollow plastic member with a U-shaped base and a sidewall curved upwardly and inwardly to form a cover which is form fitted to the infusion site under finger pressure and which can be taped in place.

9 Claims, 2 Drawing Sheets

INFUSION SITE GUARD

The present invention relates to a guard for peripheral and central venipuncture infusion sites.

BACKGROUND OF THE INVENTION

Intravenous infusion is the therapeutic introduction of a fluid, such as a saline solution, into a vein for the treatment of a wide variety of different health problems. On the human body, there are a number of possible venipuncture sites. There are peripheral venipuncture sites on the scalp, upper extremity and lower extremity and there are central venipuncture sites which access the vena cava.

The major superficial veins of the scalp are the frontal, superficial temporal, posterior auricular, supraorbital, occipital and posterior facial. In the upper extremity, venipuncture sites include the cephalic, median basilic and median antecubital veins in the forearm. In the dorsum of the hand, the commonly used veins include tributaries of the cephalic and basilic veins, as well as the dorsal venous arch. The saphenous veins, the median marginal veins and the veins of the dorsal arch of the extremities are also used.

Central venipuncture sites include the external jugular, the internal jugular or the subclavian vein. The inferior vena cava is entered through the femoral vein.

The selection of a site depends on a host of considerations including the age of the patient, condition of the patient, what kind of fluid is to be infused, rate at which the fluid is to be infused and so forth. In general, if the patient is an adult, the best venipuncture sites, in order of preference, are the lower arm and hand, the upper arm, and the antecubital fossa. If the patient is an infant, a scalp vein may be used because it is accessible and easy to protect.

Needles and catheters of various sorts are used for intravenous infusions. In the past the same needle used to puncture the vein was also used for infusing the fluid. Present practice, however, is to infuse the fluid through a catheter that is planted with a needle which is then withdrawn. Currently there are two major types of catheters—namely, over-the-needle catheters and through-the-needle catheters. A third type, butterfly needles, formerly used in treating children, have been superseded by over-the-needle catheters.

Old fashioned needles and modern catheters terminate in a hub for connection to a fluid supply line by means of a separable tapered part. The friction joint between the hub and the supply line sometimes becomes detached. When this happens, fluid is lost and the patient may be seriously affected beyond the value of the fluid lost. Needles and catheters are also subject to inadvertent displacement whereby the needle or catheter is withdrawn from the vein or perforates the vein's opposite wall causing the infusion fluid to infiltrate the surrounding tissue and it to swell. This thwarts infusion therapy and causes other problems. Displacement of the needle or catheter is particularly likely when the venipuncture infusion site is adjacent a joint.

The simplest way to stabilize the joint between the hub and the supply line and to prevent the needle and catheter from being displaced is with adhesive tape. The supply line is taped to the patient with a small loop giving the tubing more play and making the needle or catheter less likely to become dislodged if the tubing is accidentally pulled. If the venipuncture site is adjacent a joint, the joint is often immobilized.

In addition to tape, various devices have been proposed for guarding the needle or catheter at the infusion site and for protecting the joint between the needle or catheter and the supply line. Many of these devices are specially designed for use at a particular infusion site and are big, expensive and mechanically complicated. For example, there are devices with domes over the infusion site and with means for immobilizing the elbow joint for intravenous infusion adjacent the joint of an adult. There are other special purpose devices for protecting the infusion site on a child's scalp and so forth.

If the site is taped but otherwise unguarded, the catheter may still be accidentally dislodged or, in the case of adult patients with impaired senses and pediatric patients, pulled out by the patient or one of his visitors. A taped but otherwise uncovered infusion site may frighten pediatric patients and be a stressor even to adults, particularly if they are very old or sick.

There are several general purpose guards on the market for covering the infusion site (i.e., not designed to fit a particular venipuncture site). One of them is sold by Consolidated Medical Equipment, Inc. under the name "Veni-Gard" and another is sold by Mac Lee Medical Products under the name "IV Induction Cover". The Veni-Gard device for securing I.V. needles is a clear piece of plastic in a frame treated with adhesive. The frame is positioned over the infusion site and stuck to the patient with the adhesive. While the clear piece of plastic covers the site, it does not cushion the needle or catheter from above. The IV Induction Cover sold by Mac Lee is a generally clear plastic cup with a hole in its sidewall and a flanged lip treated with adhesive. The supply line is passed through the hole in the cup and the cup is fitted over the infusion site and stuck to the patient with the adhesive. While the IV Induction Cover is somewhat flexible, the flange keeps it from being universally useful. When the cup is removed, the supply line tends to jiggle the needle or catheter.

Because of the problems with commercially available guards, many nurses jury-rig I.V. covers from a urine specimen cup or the like. The cup is cut in half vertically (or horizontally depending on the application) and the cut edges wrapped with adhesive tape. It takes a nurse several minutes to make a taped half-cup and it is a very poor use of nursing time, particularly when the staff has a heavy patient load. In addition, the cover is not universally useful at all venipuncture sites or on all patients (e. g., pediatric patients) because it is stiff and will not conform to the site.

In view of the above, there is a continuing need for a general purpose guard for an infusion site which can be used at peripheral and central venipuncture infusion sites and on pediatric and adult patients.

OBJECTS AND SUMMARY OF THE INVENTION

It is an object of the invention to provide a general purpose guard for an infusion site which can be used at peripheral and central venipuncture infusion sites and on pediatric and adult patients. Other objects and features of the invention will be in part apparent and in part pointed out hereinafter.

The foregoing objects are satisfied with an infusion site guard comprising a hollow member having a U-shaped base with a generally planar lower edge. The U-shaped base is preferably outwardly flared to facilitate spreading of the U-shaped base to conform the guard to the venipuncture site to be protected. The lower edge is positioned upon the skin of a patient adjacent to a needle or catheter inserted into a vein through a venipuncture site. The lower edge of the base has means for spreading the weight of the guard across the skin, for example, by providing a smooth lower edge. The U-shaped base has a width sufficient to straddle the needle or catheter and a length sufficient to cover the needle or catheter above the infusion site. The U-shaped base is joined to a sidewall curved upwardly and inwardly to form a cover with an open and a closed end. The sidewall is preferably curved at the open end of the cover as it joins the base to avoid gouging the patient's skin when the U-shaped base is spread. The guard is formed of plastic material stiff enough to cushion the needle or catheter from a blow and flexible enough such that the U-shaped base can be spread when finger pressure is applied to the cover. The plastic material is preferably transparent or semitransparent so that the infusion site can be visualized through the cover.

In some instances, a means for retaining a strip of adhesive tape used to tape the guard to the patient is provided in the cover between the open and closed ends of the cover. The means for retaining the strip of adhesive tape preferably is a channel formed in the plastic cover.

BRIEF DESCRIPTION OF THE DRAWINGS

In the accompanying drawings, in which one of various possible embodiments of the invention is illustrated, corresponding reference characters refer to corresponding parts throughout the several views of the drawings and in which.

DETAILED DESCRIPTION OF THE INVENTION

Figure 1:
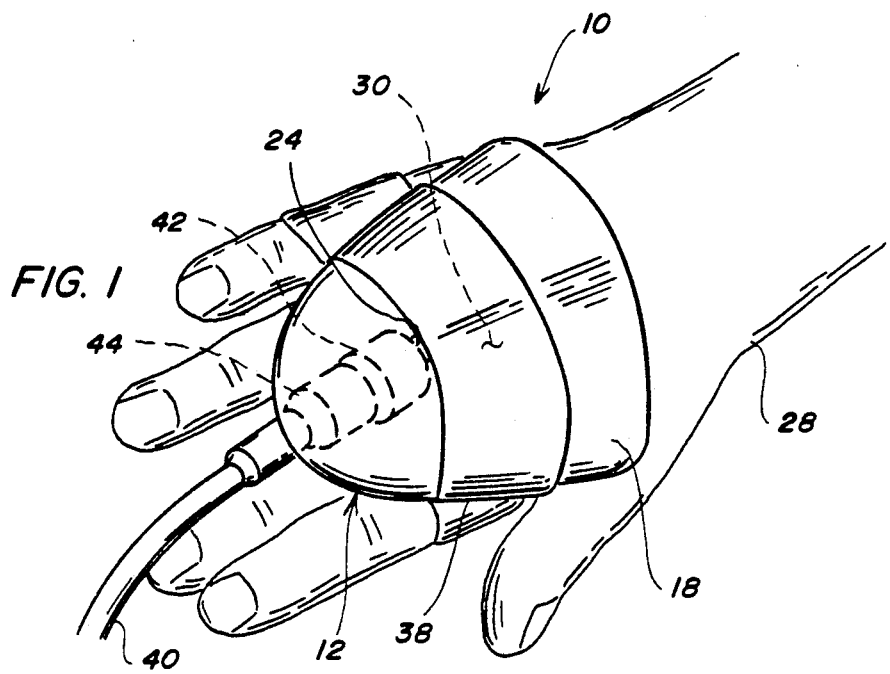
FIG. 1 is a perspective view of an infusion site guard in accordance with the present invention in use on the hand of an infant.

Referring to the drawings more particularly by reference character, reference numeral 10 refers to an infusion site guard in accordance with the present invention. Guard 10 is structurally simple but functionally elegant. It comprises a hollow member having a U-shaped base 12 with a generally planar lower edge 14. U-shaped base 12 is joined to a sidewall 16 curved upwardly and inwardly to form a cover 18 with an open end 20 and a closed end 22.

As shown in the drawings, U-shaped base 12 has a width sufficient to straddle a needle or catheter 24 inserted into a vein 26 of a patient 28 through a venipuncture site 30. U-shaped base 12 has a length sufficient to cover needle or catheter 24 above infusion site 30 and a height sufficient to provide a space between the inside of cover 18 and needle or catheter 24. Lower edge 14 has a means 32, such as a smooth lower edge, a tear drop shaped bead or the like, for spreading the weight of guard 10 across the patient's skin on which it is placed.

Figures 2, 3, 4, 5, 6:
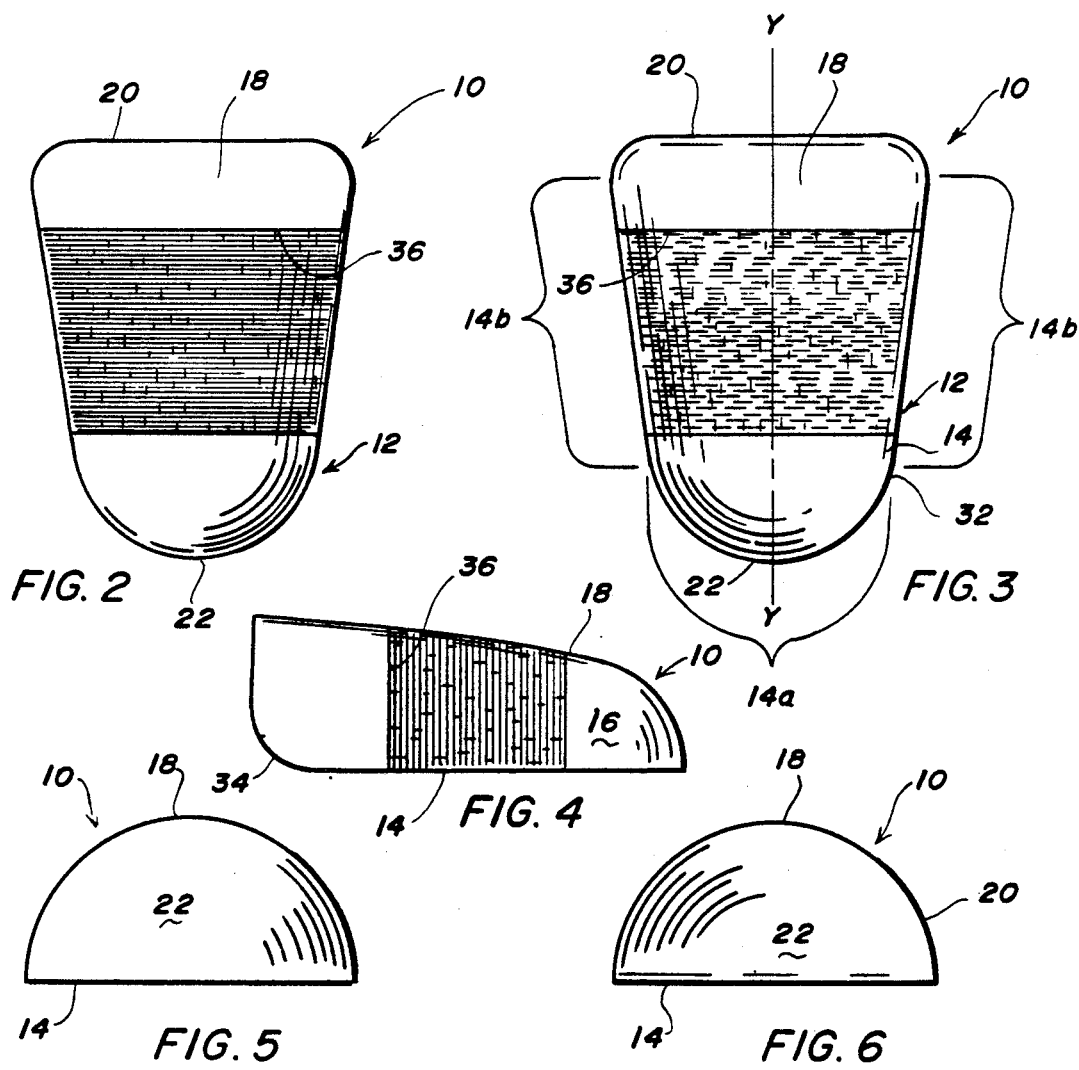
FIG. 2 is a top view of the infusion guard shown in FIG. 1.
FIG. 3 is a bottom view of the infusion guard.
FIG. 4 is a side elevation of the infusion guard.
FIG. 5 is an end elevation from the closed end of the cover.
FIG. 6 is an end elevation from the open end of the cover.
Figure 7:
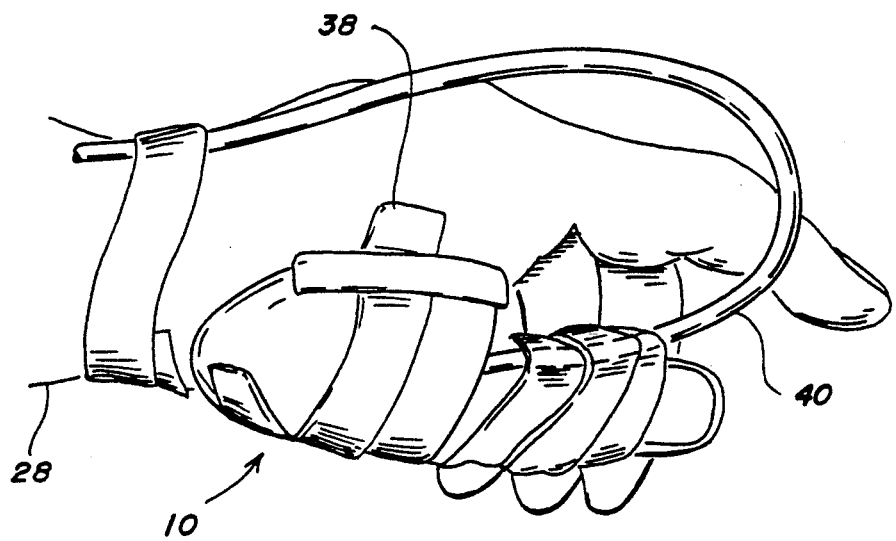
FIG. 7 is a perspective view of the infusion site guard in use on the cephalic vein in a hand.
Figure 8:
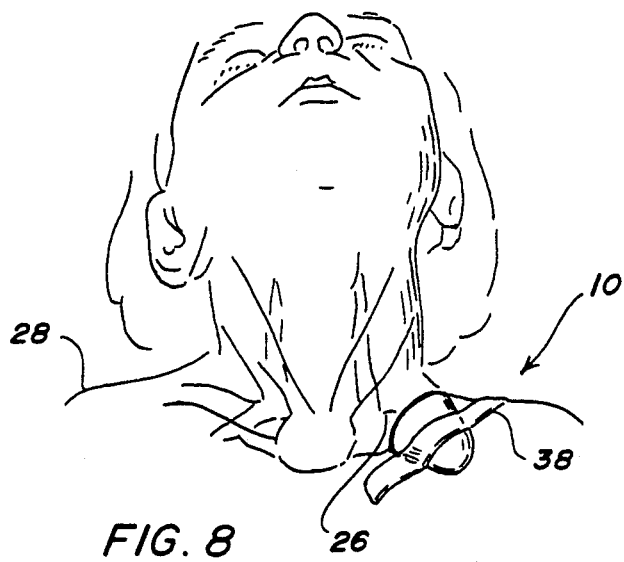
FIG. 8 is a perspective view of the infusion site guard in use on the subclavian vein of an adult; and, FIG. 9 is a frontal view of the infusion site guard in use on the dorsal venous arch of the foot.
Figure 9:
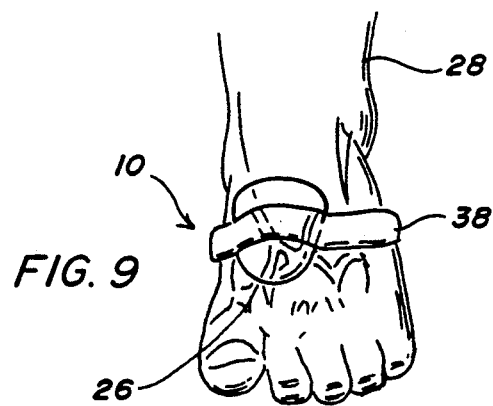

To facilitate spreading of U-shaped base 12 to conform the guard to the venipuncture site and to avoid gouging the patient's skin, it is preferred that the U-shaped base be outwardly flared (i.e., as shown in FIG. 3, planar lower edge 14 of U-shaped base 12 has a curved bottom portion 14a and a pair of longitudinal portions 14b angled outwardly from the curved bottom portion 14a with respect to a longitudinal axis Y—Y) and that sidewall 16 be curved 34 at open end 20 of cover 18 as it joins base 12.

Guard 10 is provisioned with a means 36 for retaining a strip of adhesive tape 38 used to tape the guard to patient 28. Means 36 is located in the cover between open end 20 and closed end 22 of the plastic cover. In the embodiment illustrated in the drawings, means 36 is a channel formed in the plastic cover.

Under the protection of cover 18, a supply line 40 is connected to a hub 42 of needle or catheter 24 by means of a separable tapered part 44. For intermittent use, hub 42 can be capped with a plug (not shown) and supply line 40 disconnected.

Guard 10 is formed of a plastic material stiff enough to cushion needle or catheter 24 from a blow and flexible enough such that U-shaped base 12 can be spread when finger pressure is applied to the cover.

For the purpose of visualizing the infusion site through cover 18, it is preferred that the plastic material be transparent or semi-transparent. Transparency is important since guard 10 not only acts as an enclosure but also as a window through which visual inspection may be made of needle or catheter 24, the entrance of the needle or catheter 24 into the body, and the condition of the skin surface immediately around the needle or catheter.

One suitable plastic material which satisfies the above-mentioned specifications is medical grade low density polyethylene from which a satisfactory guard 10 0.030 inch thick is manufactured by injection molding and thermoforming.

In use as shown in FIGS. 1 and 7-9, guard 10 conforms to all venipuncture sites on adults as well as infants. The flexibility of the plastic cushions any blow on cover 18 with a gradual resistance such that the friction joint between hub 42 and tapered part 44 is not broken and needle or catheter 24 is protected from displacement. There is a decreased chance of snagging needle or catheter 24 which gives the patient a sense of security. Guard 10 slides easily under covers and loose clothing, where it can be worn (such as by an AIDS patient between treatments) without detection.

To inspect the infusion site directly, tape 38 is removed from one side of guard 10, leaving the tape on the other side as a hinge. After inspection, tape 38 is reconnected. By protecting the infusion site, while leaving it readily available for inspection either through the cover or with the cover removed, the number of I.V. restarts is reduced. The reduction in I.V. starts reduces patient discomfort and lowers medical costs.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed is:

1. An infusion site guard comprising a hollow member having a U-shaped base with a generally planar lower edge to be positioned upon the skin of a patient adjacent to a needle or catheter inserted into a vein through a venipuncture site, said lower edge having means for spreading the weight of the guard across the skin, said lower edge having a curved bottom edge portion and a pair of longitudinal edge portions angled outwardly from the bottom edge portion, said U-shaped base having a width sufficient to straddle the needle or catheter and a length sufficient to cover the needle or catheter above the infusion site, said U-shaped base joined to a sidewall curved upwardly and inwardly to form a cover having a hollow space with an outer perimeter which substantially coincides with the lower edge and with an open and a closed end, said guard formed of a plastic material stiff enough to cushion the needle or catheter from a blow and flexible enough such that the U-shaped base can be spread when finger pressure is applied to the cover to conform the guard to the venipuncture site to be protected.

2. The guard of claim 1 wherein the sidewall is curved at the open end of the cover as it joins the base to avoid gouging patient's skin when the U-shaped base is spread.

3. The guard of claim 2 wherein the infusion site can be visualized through the cover.

4. The guard of claim 1 wherein a means for retaining a strip of adhesive tape used to tape the guard to the patient is provided in the cover between the open and closed end of the cover.

5. The guard of claim 4 wherein the means for retaining the strip of adhesive tape is a channel formed in the plastic cover.

6. An infusion site guard comprising a hollow member having a U-shaped base with a generally planar lower edge to be positioned upon the skin of a patient adjacent to a needle or catheter inserted into a vein through a venipuncture site, said lower edge smooth for spreading the weight of the guard across the skin, said lower edge having a curved bottom edge portion and a pair of longitudinal edge portions angled outwardly from the bottom edge portion, said U-shaped base having a width sufficient to straddle the needle or catheter and a length sufficient to cover the needle or catheter above the infusion site, said U-shaped base joined to a sidewall curved upwardly and inwardly to form a cover having a hollow space with an outer perimeter which coincides with the lower edge and with an open and a closed end, said sidewall curved at the open end of the cover as it joins the base to avoid gouging the patient's skin when the U-shaped base is spread, said guard formed of a plastic material stiff enough to cushion the needle or catheter from a blow and flexible enough such that the U-shaped base can be spread when finger pressure is applied to the cover.

7. The guard of claim 6 wherein a means for retaining a strip of adhesive tape used to tape the guard to the patient is provided in the cover between the open and closed end of the cover.

8. The guard of claim 7 wherein the means for retaining the strip of adhesive tape is a channel formed in the plastic cover.

9. The guard of claim 8 wherein the infusion site can be visualized through the cover.

* * * * *